(12) United States Patent
Singh

(10) Patent No.: US 8,192,196 B2
(45) Date of Patent: Jun. 5, 2012

(54) OSTEOGENETIC-PNEUMOPEDIC APPLIANCE, SYSTEM, AND METHOD

(76) Inventor: Gurdev Dave Singh, Portland, OR (US)

( * ) Notice: Subject to any disclaimer, the term of this patent is extended or adjusted under 35 U.S.C. 154(b) by 276 days.

(21) Appl. No.: 12/601,918

(22) PCT Filed: Oct. 14, 2009

(86) PCT No.: PCT/US2009/060579
§ 371 (c)(1),
(2), (4) Date: Nov. 25, 2009

(87) PCT Pub. No.: WO2010/045279
PCT Pub. Date: Apr. 22, 2010

(65) Prior Publication Data
US 2011/0269095 A1    Nov. 3, 2011

Related U.S. Application Data

(60) Provisional application No. 61/106,117, filed on Oct. 16, 2008.

(51) Int. Cl.
*A61C 3/00* (2006.01)
(52) U.S. Cl. .......................................................... 433/7
(58) Field of Classification Search ................. 433/6–7, 433/18–24; 128/848
See application file for complete search history.

(56) References Cited

U.S. PATENT DOCUMENTS

| | | | | |
|---|---|---|---|---|
| 4,026,023 A | * | 5/1977 | Fisher | 433/7 |
| 4,229,165 A | * | 10/1980 | Kurz | 433/24 |
| 4,976,614 A | * | 12/1990 | Tepper | 433/18 |
| 5,096,416 A | * | 3/1992 | Hulsink | 433/6 |
| 5,580,243 A | * | 12/1996 | Bloore | 433/6 |
| 5,816,800 A | * | 10/1998 | Brehm et al. | 433/7 |
| 5,829,970 A | * | 11/1998 | Yousefian | 433/7 |
| 6,604,943 B2 | * | 8/2003 | White | 433/21 |
| 7,314,372 B2 | | 1/2008 | Belfor et al. | |
| 7,357,635 B2 | | 4/2008 | Belfor et al. | |
| D600,350 S | | 9/2009 | Singh | |
| 2005/0261679 A1 | * | 11/2005 | Belfor et al. | 606/57 |
| 2007/0264605 A1 | | 11/2007 | Belfor et al. | |

FOREIGN PATENT DOCUMENTS

WO    WO2009/045933    4/2009

OTHER PUBLICATIONS

Singh, G. D., Diaz, J., Busquets-Vaello, C., and Belfor, T. R. "Soft tissue facial changes following treatment with a removable orthodontic appiance in adults." published in Funct. Orthod. (2004) vol. 21, No. 3.

* cited by examiner

*Primary Examiner* — Cris L Rodriguez
*Assistant Examiner* — Hao D Mai
(74) *Attorney, Agent, or Firm* — Peter A Haas Esquire LLC

(57) ABSTRACT

One embodiment of the present invention consists of a non-rigid, epigenetic-pneumopedic appliance comprising a wire-type framework supporting bow, bands, brackets or a clasp. The appliance includes active elements adapted to provide brief doses of cyclic forces to induce sutural osteogenesis. The active elements are vibrational, ultrasonic or oscillatory components. The epigenetic-pneumopedic appliance cooperates with an actuator or other expansion mechanism, such as suture spring, that straddles the midline of the appliance. The appliance further includes tooth-contacting material having high-elasticity, such as pre-formed alloys that form 3-D axial springs, which adapt to the long axis of the palatal/lingual surfaces of the teeth. The appliance also includes a plurality of micro-screws 2 along with driving means preferably consisting of either an electrical, ultrasonic (vibrational) meso-motor, or, alternatively, a micro-motor. The epigenetic-pneumopedic appliance may be used with directional bite props.

8 Claims, 13 Drawing Sheets

15b

15a

OSTEOGENETIC-PNEUMOPEDIC APPLIANCE, SYSTEM, AND METHOD

PRIORITY CLAIM

The present invention, being filed as a Patent Cooperation Treaty application, claims benefit for all purposes, including benefit under 35 USC Section 119(e), of U.S. Provisional Patent Application No. 61/106,117 filed on 16 Oct. 2008 entitled "Osteogenetic-Pneumopedic Appliance, System, and Method" by the common inventor Gurdev Dave Singh.

BACKGROUND

The present invention relates to devices, systems, and treatment methods directed at aligning and correcting orthodontic or dentofacial and/or mild craniofacial variations, including both foundational correction (a treatment that changes the skeletal and/or dental tissues) and functional correction (a treatment that changes the soft tissues and/or tissue spaces).

More specifically, the present invention relates to clinical protocols, devices, systems, and methods incorporating osteogenetic-pneumopedic and/or osteogenetic-orthodontic appliances. Osteogenetic-pneumopedic and osteogenetic-orthodontic appliances are specialized orthopedic and/or orthodontic appliances that signal the genome of the patient to non-surgically remodel tissues and spaces, for example via a patient's own, inherent stem cells. Osteogenetic-pneumopedic treatment provides an integrated patient management system using a multi-disciplinary approach, incorporating devices, systems, and methods directed at aligning and correcting orthodontic, dentofacial and/or mild craniofacial variations, using both foundational correction and functional correction, including non-surgical airway-remodeling.

The cranio-caudal gradient of human development theory teaches that the cranium develops before the midface, which develops before the mandible etc. Current and existing treatment methods and appliances teach the use of compartmentalized patient management. And, specifically, the current art teaches that common craniofacial abnormalities are suitably corrected by using well-known devices and treatment methods that include surgery, injections and drugs.

Common orthodontic, dentofacial and craniofacial abnormalities are typically corrected for both esthetic and medical reasons. Reasons include, for example, the perception that a well-balanced face is beautiful and correlates with minimal or no craniofacial health problems. Common health problems associated with unbalanced, unhealthy faces include, for example: Deformational or positional plaigocephaly; mouth-breathing; dental malocclusions; bruxism (including, grinding, clenching and tooth wear); facial underdevelopment (including facial asymmetry and craniofacial obesity); temporomandibular joint dysfunction (TMD); and upper airway difficulties and sleep disordered breathing, such as snoring, upper airway resistance syndrome and obstructive sleep apnea (OSA). These conditions, whether diagnosed or covert, represent major issues in this field of work. In addition, a well-balanced face may be more resistant to head injury, such as concussion or mild traumatic brain injury, either during sport or in other physical activities.

Although traditional devices and treatments attempt to correct the esthetic problems, they do not adequately address underlying causes of poor craniofacial homeostasis. Poor craniofacial homeostasis is commonly accompanied by several other clinically observable signs and symptoms, such as cranial asymmetry and facial asymmetry, airway issues etc., according to the patient's genome.

For example, one major issue not adequately addressed in the current art teachings and traditional methods and devices is the irregular alignment of the cranium, jaws and teeth as a result of development compensation. For example, malocclusion, an obvious sign of which is irregular teeth, belies a more serious issue, and may require correction of the soft tissues (e.g. the tongue) and/or development of the bone constituting the cranium, including the jaws, during comprehensive, integrated, multi-disciplinary care.

Further, the current teachings in this art do not fully treat the underlying causes of developmental compensation. The current art does not provide treatment methods or devices that adequately interact with or naturally-manipulate the patient's genome via stem cells. Due to an overall lack of recognizing the importance of the impact of the environment acting on a patient's genes, traditional methods and devices lack structural elements and clinical protocols necessary to properly signal or interact more appropriately with a patient's genes via stem cells. This results in less than optimal corrections despite the current-art's attempt at invoking temporo-spatial patterning or the genetic template of craniofacial development.

Examples of common but detrimental environmental stimuli not properly addressed by the current art include: Postural influences, such as excessive laying down of a newborn baby on its back, deficient holding of a baby/infant, or excessive baby/infant car seat use; and Myofunctional influences, such as a lack of breast-feeding, bottle-feeding, pacifier use, digit-sucking, or other childhood habits, including a soft diet of refined foods.

Other genome-related and environmental-influenced abnormalities not adequately addressed in the current art include certain features of deformity, such as cranial asymmetry, and dysfunctional features, including adverse tongue posture, abnormal swallowing patterns and lip activity, which lead to further craniofacial consequences as the child matures. One further craniofacial consequence during maturation includes malocclusion. Additionally, some consequences, for example obstructive sleep apnea or a predisposition to concussion, may not manifest until early or late adulthood.

These aforementioned consequences are the outcomes of gene-environmental interaction factors that—according to recent studies—perturb the genetic, craniofacial foundation encoded by genes. The perturbed features include cranial asymmetry, a high-vaulted palate with maloccluded teeth, and other dysfunctional features, such as a submandibular pannus (double chin) or unerupted wisdom teeth, etc. Further, the complexity of these gene-environmental interactions leads to heterogeneity. Thus, a given patient may present a single feature such as a lisp, malocclusion, TMD, snoring, wear facets on teeth, aged facial appearance or any combination of the above, even though the underlying etiology is similar.

According to the teaching of the current state-of-the art, these perturbed features and abnormalities are well adapted to corrective treatments, for example using appliances that utilize biomechanical loading. Biomechanical loading, as taught by the current state-of-the-art, is an important regulator of osteogenesis. Osteogenesis recognizes that bone formation occurs in response to its functional environment and, accordingly, biomechanical loading using biophysical techniques of osteo-stimulation can be successful when used in a clinical practice. These clinical, biophysical techniques include surgical, craniofacial distraction osteogenesis, and the application of ultrasound to promote bone formation, for example.

Sutures, another known structure adapted to correct craniofacial features and abnormalities in the current art, are fibrous connective tissue articulations found between intramembranous craniofacial bones. They consist of multiple connective tissue cell lines such as mesenchymal cells, fibroblasts, osteoclasts and osteogenic cells derived from stem cells. Sutures are organized with stem cells. For example, osteogenic cells differentiate at the periphery, producing a matrix that is mineralized during bone growth and development; fibroblastic cells are found with their matrices in the center.

Cyclic loading of sutures has clinical implications and act as mechanical stimuli for modulating craniofacial growth and development in patients. One study demonstrated that in vivo mechanical forces regulate sutural growth responses in rats. In that study, cyclic compressive forces of 300 mN at 4 Hz were applied to the maxilla for 20 min/day over 5 consecutive days. In that study, computerized analysis revealed that cyclic loading significantly increased the average widths of the sutures studied in comparison with matched controls, and the amount of osteoblast-occupied sutural bone surface was significantly greater in cyclically loaded sutures.

Thus, studies demonstrate that cyclic forces are potent stimuli for modulating postnatal sutural development, potentially by stimulating both bone formation (osteogenesis) and remodeling (osteoclastogenesis). Therefore, craniofacial sutures have capacities for mechanical deformation, and the elastic properties of sutures may potentially play a useful role in improving the craniofacial health of a patient through continued craniofacial development via stem cells.

Current data on suture mechanics suggest that mechanical forces regulate sutural growth by inducing sutural mechanical strain. Therefore, various therapies, including osteogenetic-pneumopedic and/or osteogenetic-orthodontic appliances, may induce sutural strain, leading to modifications of natural sutural growth. For example, Singh G. D., Diaz, J., Busquets-Vaello, C., and Belfor, T. R. in "Soft tissue facial changes following treatment with a removable orthodontic appliance in adults," Funct. Orthod., (2004) vol. 21 no. 3 at pp. 18-23, reported dental and facial changes in adults treated with a rigid, static, removable orthodontic appliance (and as disclosed in U.S. Patent Application No. 2007/0264605 published on 15 Nov. 2007, and as disclosed in U.S. Pat. Nos. 7,314,372 issued on 1 Jan. 2008 and 7,357,635 issued on 15 Apr. 2008, the full disclosures of which are hereby incorporated by reference as if set out fully herein). Furthermore, Singh G. D., Garcia A. V. and Hang W. M. in "Evaluation of the posterior airway space following Biobloc therapy: Geometric morphometrics" in the Journal of Craniomandibular Practice 25(2): 84-89, 2007, reported non-surgical airway remodeling in children treated with a rigid, static, removable orthodontic protocol. A relative 31% increase in nasopharyngeal airway area was found above and behind the soft palate. Additionally, a 23% increase in oropharyngeal airway area was located behind the base of the tongue, with a 9% increase in hypopharyngeal area near the level of the hyoid bone. Thus, functional airway improvements i.e. a pneumopedic effect is/are associated with removable orthodontic protocols in actively growing children. However, the treatment time in children was excessively long (up to 27 months) using that rigid, static, removable orthodontic protocol. Nevertheless, current orthodontic and dentofacial orthopedic therapies exclusively utilize static forces to change the shape of craniofacial bones via mechanically-induced bone apposition and resorption, but cyclic forces capable of inducing different sutural strain wave forms may accelerate sutural anabolic or catabolic responses via stem cells.

Recently, it was shown that low-intensity, pulsed ultrasound enhances jaw growth in primates when combined with a mandibular appliance, and that orthodontically induced root resorption can be repaired using ultrasound in humans.

Yet, there remains a need for improved treatment methods, systems, and devices that utilize therapies that harness the underlying developmental mechanisms—encoded at the level of the gene and realized via stem cells. Further, such improved treatment methods, devices, and systems should utilize the application of brief doses of cyclic forces to induce sutural osteogenesis via stem cells. Additionally, there remains a need for removable, non-rigid, osteogenetic-pneumopedic and/or osteogenetic-orthodontic appliances with cyclic functionality and a system and method to bioengineer vibrational osteogenetic-pneumopedic and/or osteogenetic-orthodontic devices. However, for any foundational correction to remain stable, it must be co-provided with a functional correction.

DRAWING

Figure 19:
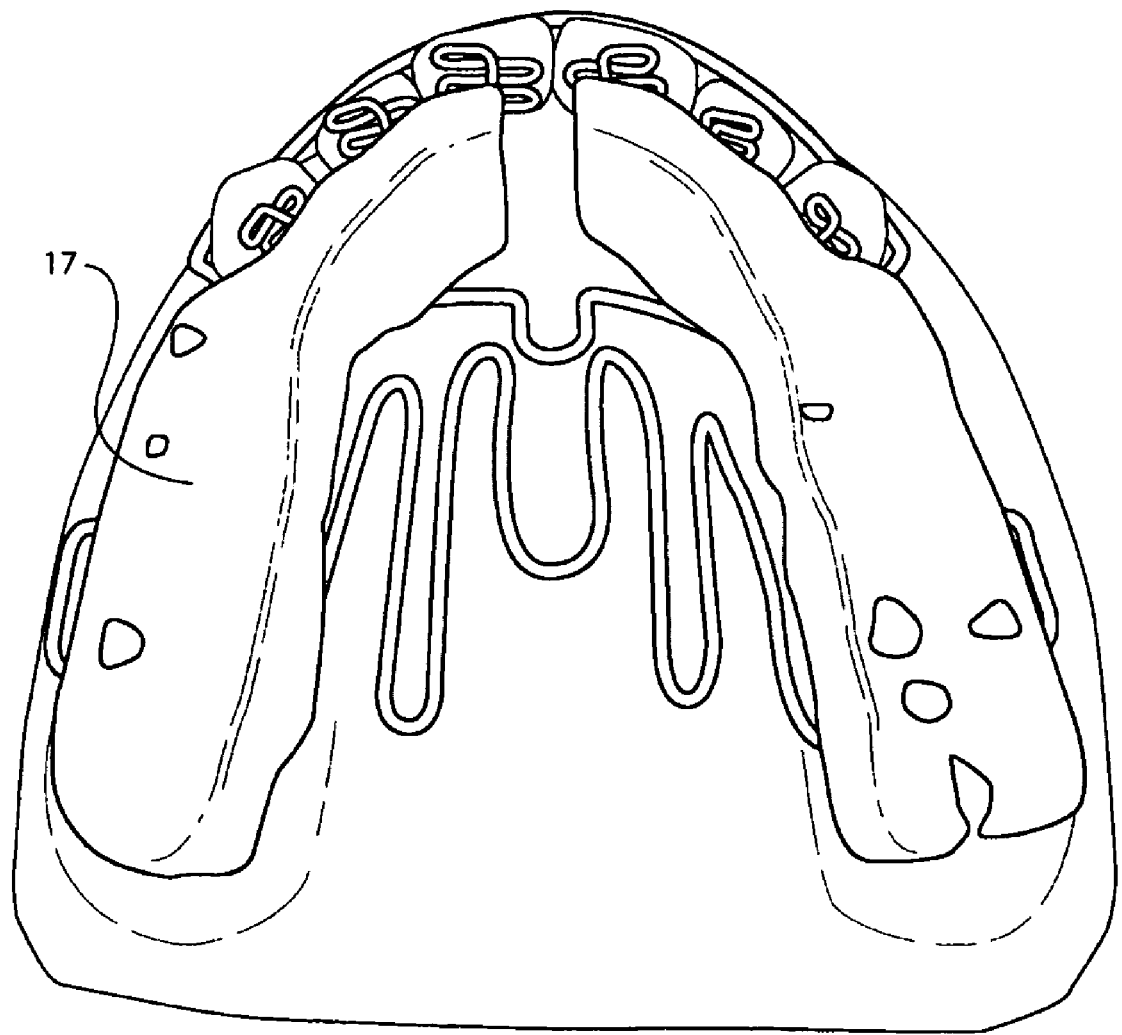

FIG. 19 is a top view of an appliance according to another preferred embodiment of the present invention, in which the directional bite props 4 are replaced by a posterior acrylic bite plane 17 in appliance 100 or 101 or 102.

DESCRIPTION OF THE INVENTION

Possible embodiments will now be described with reference to the drawings and those skilled in the art will understand that alternative configurations and combinations of components may be substituted without subtracting from the invention. Also, in some figures certain components are omitted to more clearly illustrate the invention. Further, in the various preferred embodiments similar components share a common reference number when they can be interchangeably used between embodiments. In some of the figures similar components have individual reference numbers to more clearly illustrate differences and advantages of those particular components relative to their use in a specific embodiment—however, those skilled in the art will appreciate that substitution, replacement, or interchanging the various components in the various embodiments would provide other feasible variations of the present invention and are, therefore, included implicitly in this disclosure.

The various embodiments of the present invention improve upon the teachings of the current art by providing new and improved treatment methods, systems, and appliances that utilize therapies that harness the underlying developmental mechanisms—encoded at the level of the gene and realized through stem cells—by applying brief doses of cyclic forces to induce sutural osteogenesis. Other objectives of the present invention include, but are not limited to, providing a selectively removable, osteogenetic-pneumopedic and/or osteogenetic-orthodontic appliance with cyclic functionality, and a system and method to bioengineer vibrational, osteogenetic-pneumopedic and/or osteogenetic-orthodontic devices.

One objective of the invention is to increase, enhance, optimize and augment craniofacial homeostasis, equilibrium and balance. Accordingly, the present invention includes an appliance, system, and treatment method for correcting common orthodontic, dentofacial and craniofacial variations.

Treatment Methods

In one preferred embodiment, the present invention includes a treatment method comprising the steps including: Providing a cranial examination by a suitably trained healthcare professional, such as a cranial osteopath, of a young baby soon after birth. In the event that cranial asymmetry is diagnosed, cranial osteopathy may be provided as indicated; Providing an oral examination by a suitably-trained healthcare professional, such as a general or pediatric dentist, of a young baby soon after birth. In the event that ankylosis of the tongue is diagnosed, lingual frenectomy or frenotomy may be provided as indicated; Providing an oral myofunctional examination by a suitably trained healthcare professional, such as an oral myologist or myofunctional therapist, by the age of three years (when the deciduous teeth are usually fully erupted and in occlusion). In the event that myofunctional habits, such as digit-sucking, lip-sucking etc are diagnosed, myofunctional therapy may be provided as indicated; Providing an orthodontic examination by a suitably trained healthcare professional, such as an orthodontist, pediatric or general dentist, by the age of six years (when the permanent teeth usually begin to erupt). In the event that a malocclusion is diagnosed or developing, osteogenetic-orthodontic therapy may be provided as indicated; Providing a TMJ examination by a neuromuscular dentist or general dentist, by the age of eight years. If TMD is diagnosed or developing, Phase I TMD therapy may be provided as indicated; Providing a sleep-study examination by a suitably trained healthcare professional, such as a sleep specialist, otorhinolaryngologist, pulmonologist, internist, etc., by the age of six years. In the event that sleep-disordered breathing is diagnosed, osteogenetic-pneumopedic therapy may be provided as indicated; Providing a cervical examination by a suitably-trained healthcare professional, such as a chiropractor, osteopath or other orthopedist specialist, etc. In the event that cervical lordosis, hyperlordosis or kyphosis is diagnosed even after osteogenetic-pneumopedics, appropriate therapy may be provided as indicated, in accord with the cranio-caudal gradient of human development.

Another preferred embodiment of the present invention includes a method for achieving concurrent craniofacial correction, combining simultaneous pneumopedic and orthodontic therapies without the use of typical biomechanical forces or surgery or drugs or injections of any kind. The method comprises:

(a) introducing one or more osteogenetic-pneumopedic appliance(s) into the oral cavity;

(b) altering the spatial relations or the bite of the jaws and teeth, including using directional bite props if indicated;

(c) adjusting the appliances to achieve optimal, intimate contact with the oral structures, including the teeth, but without the use of force that push or pull on the teeth;

(d) inducing an intermittent, non-continuous, cyclic stimulus or stimuli that reach a physiologic threshold to evoke mechanoreceptors on the cells and stem cells present within the periostea, craniofacial sutures, etc., including the periodontium;

(e) permitting tissue remodeling to occur such that the appliances lose intimate contact with oral structures, including the teeth; and (f) re-adjusting the appliance or appliances to re-establish optimal, intimate contact with oral structures, including the teeth.

This method is further adopted to include adjusting the amount of correction relative to an individual patient's genome. Additionally, the time of correction depends on the individual's genome. Notably, this method does not require the application of orthodontic brackets or elastics to the teeth. However, in an alternative embodiment, the present method adapts to cooperate with orthodontic brackets or elastics applied to the teeth. In yet another alternative preferred embodiment, the method adapts to cooperate with orthodontic wires and/or elastics that are applied to orthodontic brackets, which are applied to the teeth.

Figure 8:
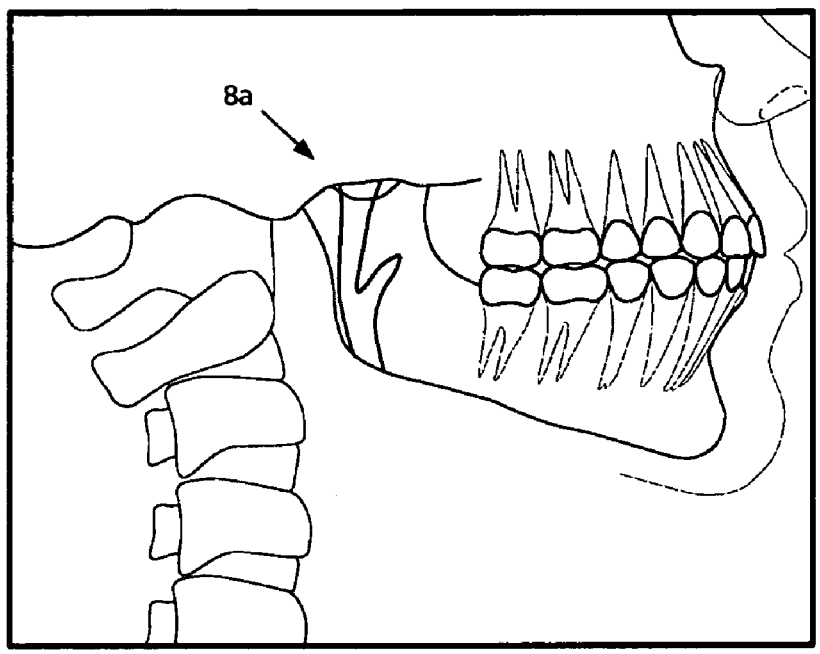
FIG. 8 shows a relatively narrow nasopharyngeal airway of a patient's upper airway before treatment.
Figure 9:
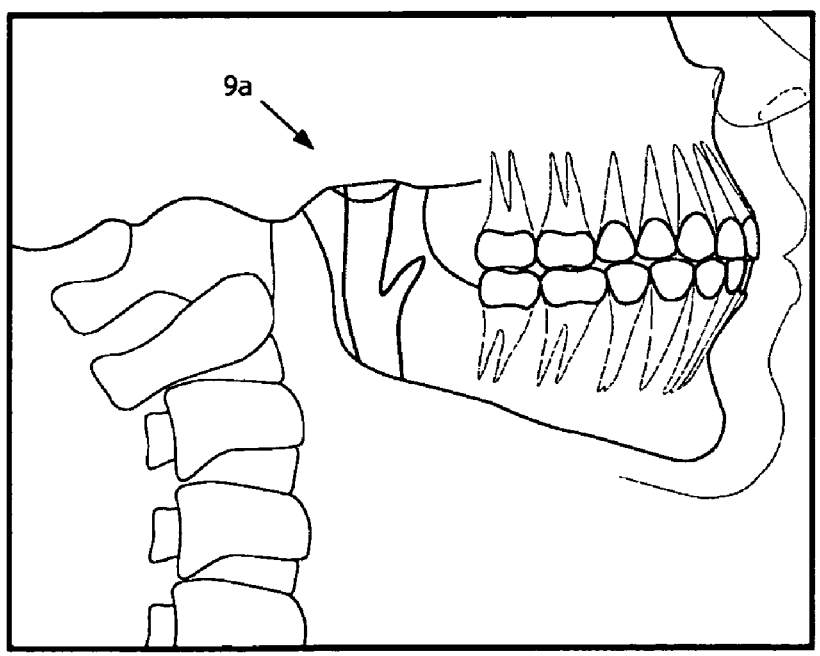
FIG. 9 shows the same patient's upper airway as in FIG. 8 after epigenetic-pneumopedic treatment.

The various treatment methods according to alternative preferred embodiments of the present invention correct relatively narrow nasopharyngeal airways in patients. For example, FIG. 8, taken from an actual x-ray of a patient, illustrates an upper airway before treatment: It will be noticed that the patient's nasopharyngeal airway is relatively narrow. Then, (taken from an actual patient x-ray) as FIG. 9 shows, the same patient's upper airway after epigenetic-pneumopedic treatment is now wider, even though this patient's upper airway was not treated by surgery, drugs or injections. While not wishing to be held to any theory of operation, it is believed that the non-surgical upper airway enhancement or pneumopedic effect is the result of remodeling of functional tissue spaces, not due entirely to the application of force to specific areas, but to the developmental mechanisms encoded at the genetic level of the patient, as predicted by the Spatial Matrix Hypothesis of Singh.

Appliance

Figure 15:
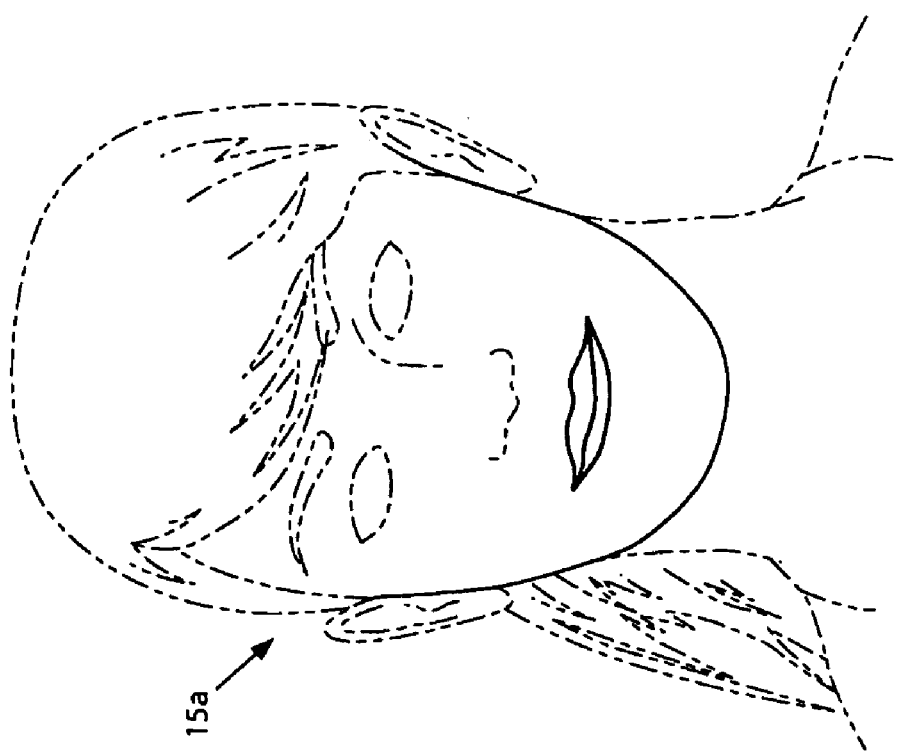
FIG. 15 shows a patient's facial appearance from the front prior to and after using appliance 100.
Figure 15:
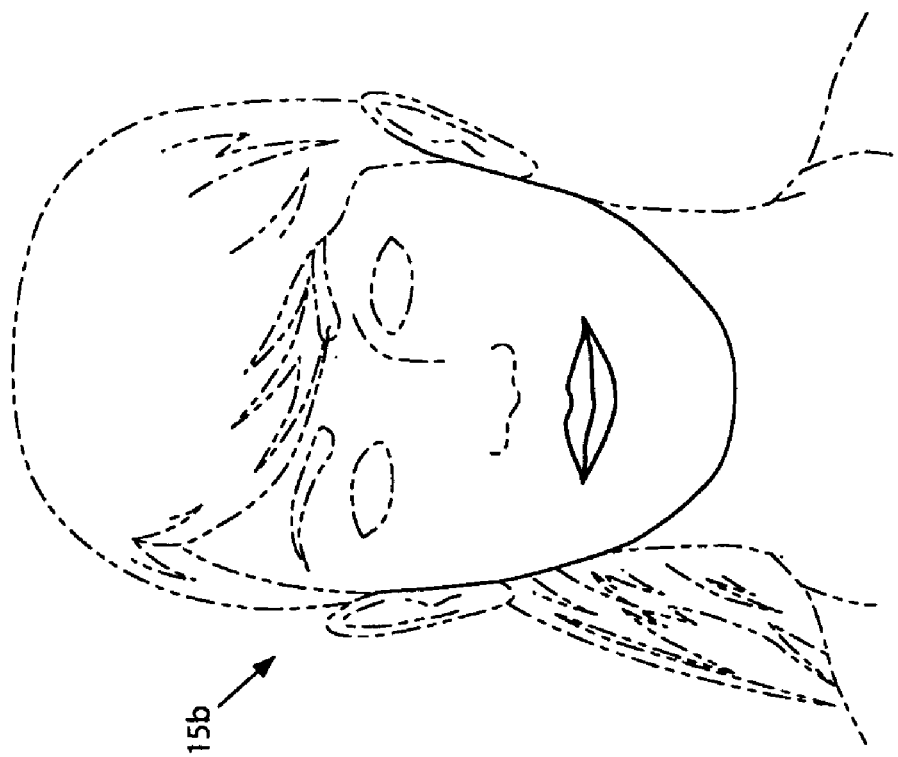

In another preferred embodiment, the present invention includes a vibrational orthopedic-orthodontic appliance adapted to induce craniofacial homeostasis by interacting with the patient's genome via stem cells. In the various preferred embodiments of the appliance discussed below, dramatic results in patients occur. For example, taken from an actual photograph of a patient, FIG. 15 represents a patient's facial appearance from the front prior to and after using appliance 100. Note the degree of facial asymmetry 15*a* (left panel) prior to using appliance 100, and the improvement in facial appearance 15*b* (right panel) after using appliance 100. Note that no surgery, drugs or injection were used to improve the facial symmetry.

Figure 16:
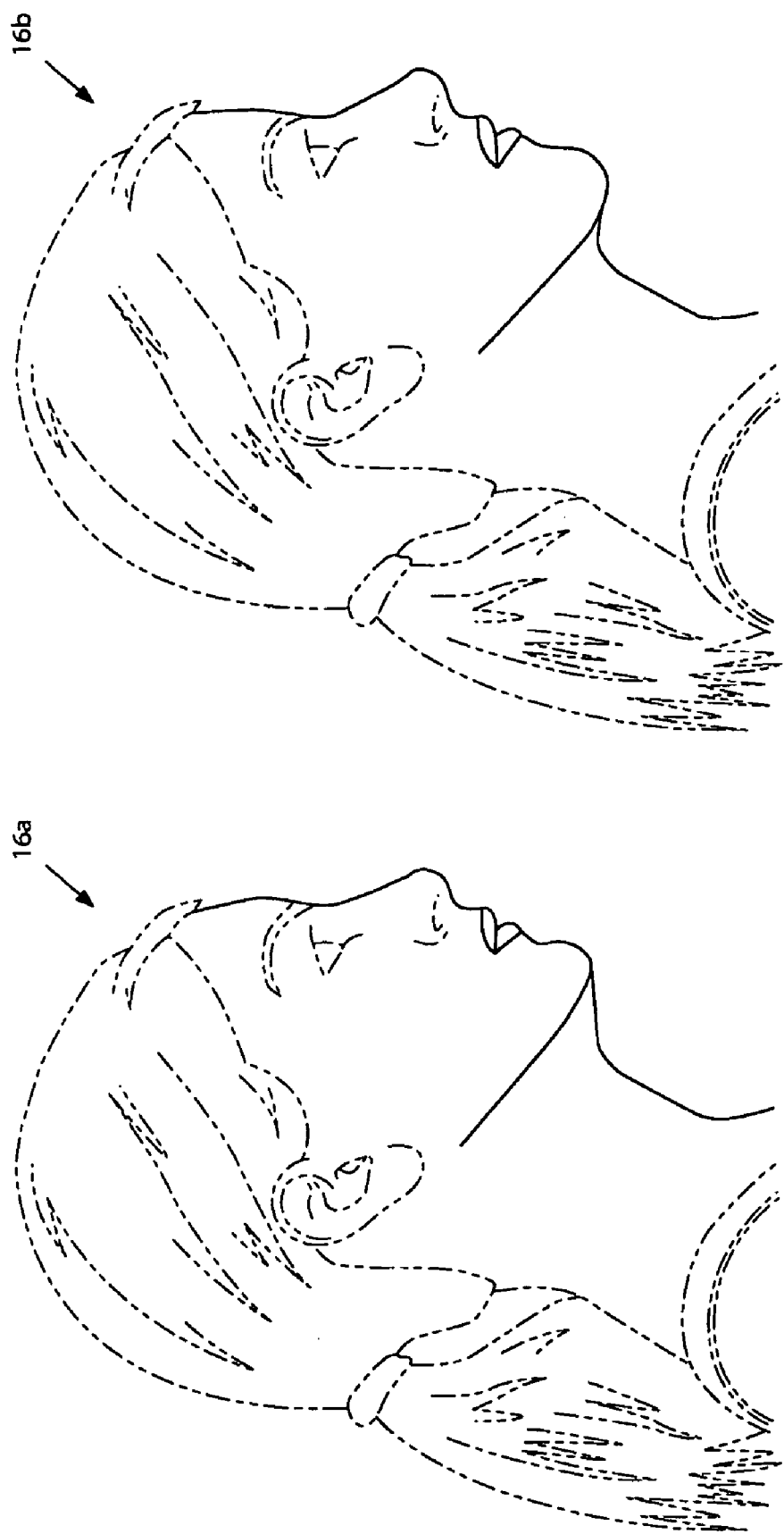
FIG. 16 shows the right side of the same patient as in FIG. 15.

The right side of the same patient was photographed and FIG. 16 represents the same patient as in FIG. 15, and shows the facial profile prior to 16*a* and after using appliance 100. Note the degree of facial underdevelopment 16*a* (left panel) prior to using appliance 100, and the improvement in facial profile 16*b* (right panel) after using appliance 100. Note that no surgery, drugs or injection were used to improve the facial profile.

Figure 17:
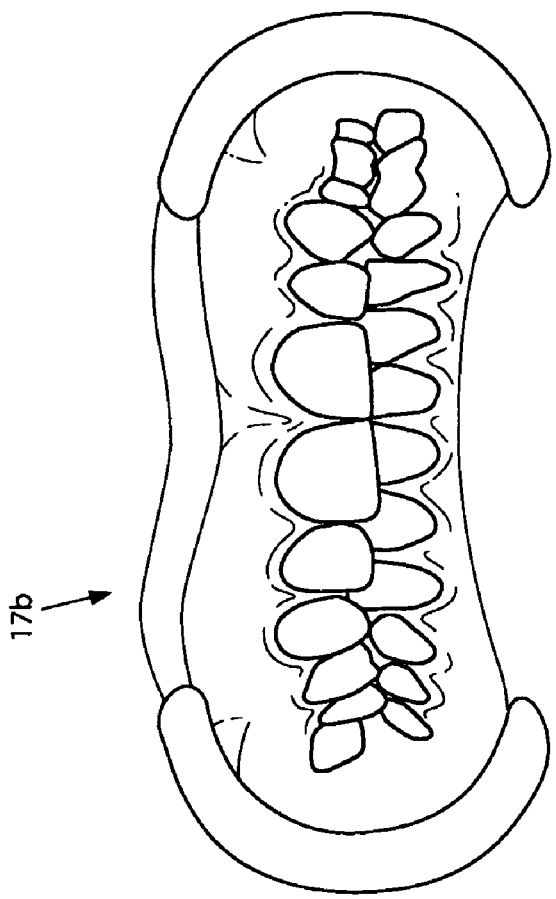
FIG. 17 shows the occlusion (bite) of the same patient as in FIG. 15 prior to and after using appliance 100.
Figure 17:
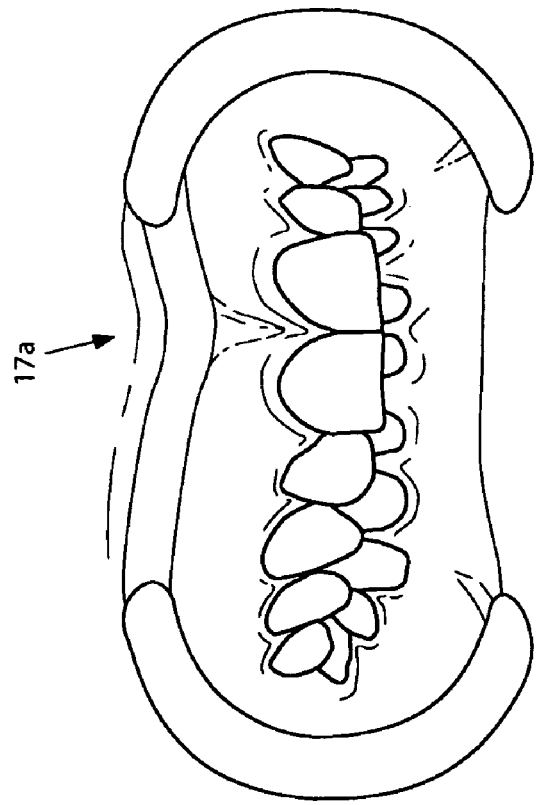
Figure 18:
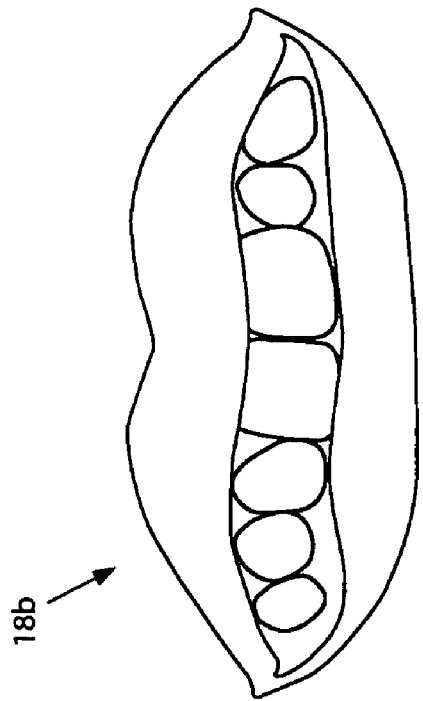
FIG. 18 shows the smile and lip line prior to and after using appliance 100 of the same patient as in FIG. 15.
Figure 18:
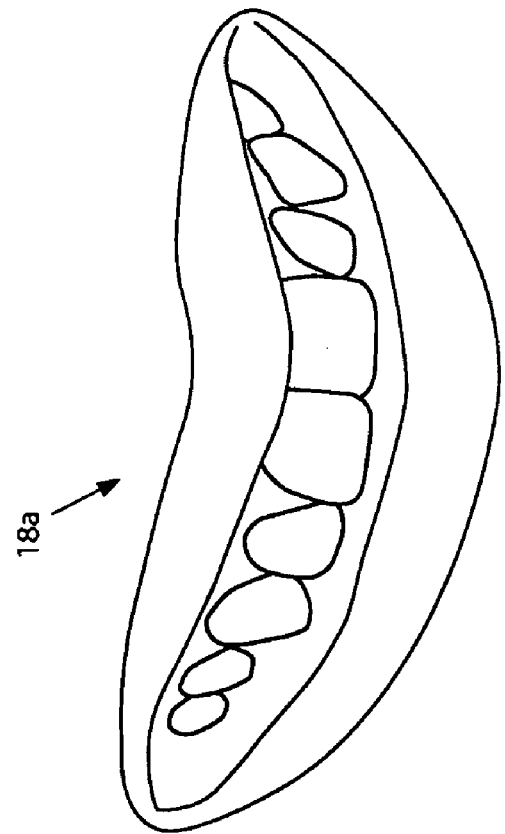

Again, the same patient's teeth where photographed and FIG. 17 represents the teeth of the same patient as in FIG. 15 and shows the occlusion (bite) prior to and after using appliance 100. Note the excessive overbite 17*a* (left panel) prior to using appliance 100, and the improvement in the overbite 17*b* (right panel) after using appliance 100. Note that no orthodontics brackets or braces or elastics, or surgery, or drugs or injection were used to improve the overbite. And, FIG. 18 (taken from a photograph of the lips of the same patient as in FIG. 15) illustrates the smile and lip line prior to and after using appliance 100. Note the underdeveloped upper lip 18*a* (left panel) prior to using appliance 100, and the improvement in the upper lip 18*b* (right panel) after using appliance 100. Note that no surgery, drugs or injection were used to improve the smile and lip line.

Archform/Body Wire

Figure 1:
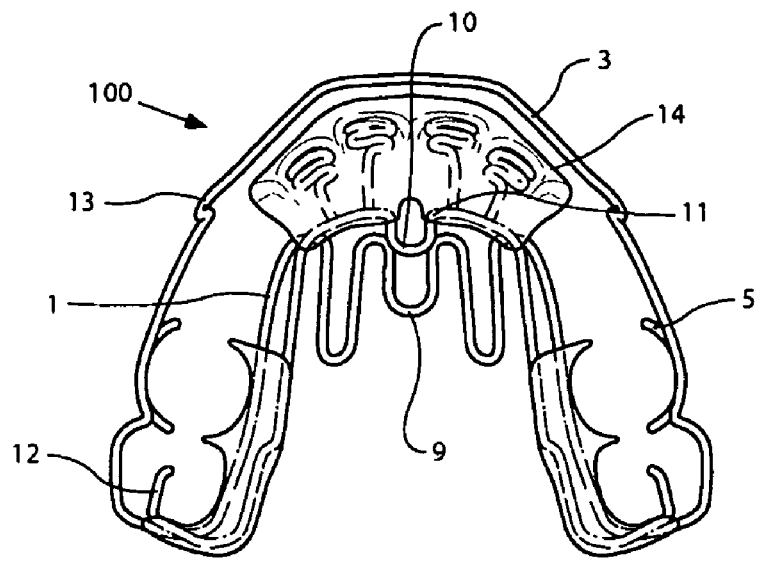
FIG. 1 is a top view of an appliance according to a first preferred embodiment of the present invention.
Figure 2:
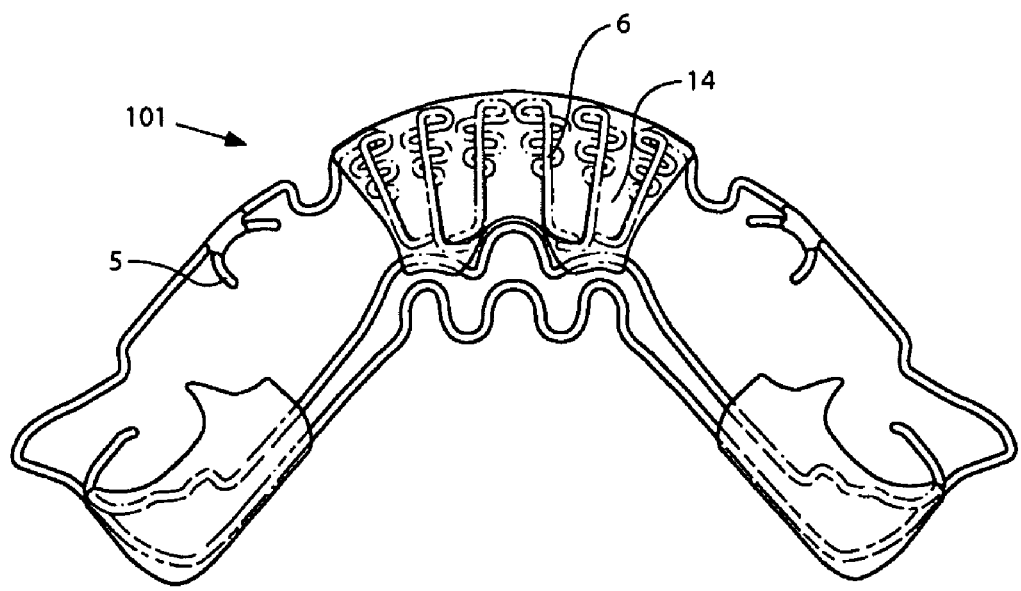
FIG. 2 is a top view of an appliance according to second preferred embodiment of the present invention.
Figure 10:
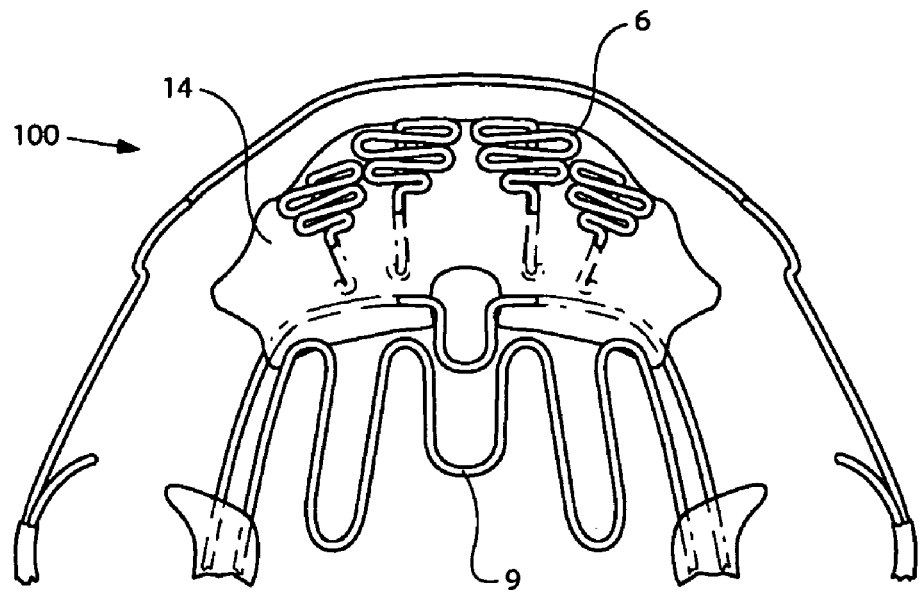
FIG. 10 is a top view of appliance 100 with an upper suture spring 9 in situ according to one preferred embodiment of the present invention.
Figure 11:
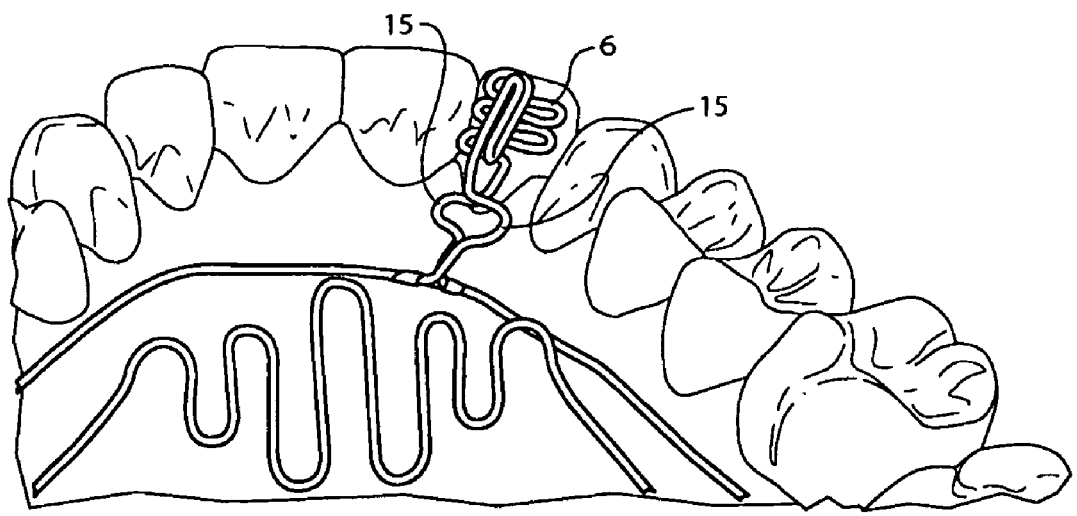
FIG. 11 is a top view of an appliance with a 3-D axial spring 6 in situ including C-loops 15, according to one preferred embodiment of the present invention.

Accordingly, one preferred embodiment of the present invention as illustrated in FIGS. 1 and 10 contemplates a removable, non-rigid, epigenetic-pneumopedic appliance without active acrylic plates. The appliance 100 consists of a wire-type framework, such as the body wire or archform 1 of FIG. 1 constructed of round wire with a diameter of approximately about 0.032 to about 0.036 inches. This framework, preferably, consists of an alloy material commonly available in the dental and orthodontic appliance art. The body wire or archform 1 serves as a base on which various components couple or are otherwise attached. For example, the body wire or archform 1 supports 3-D axial springs 6 or clasps, such as a C clasp 5 (clasp 5 is better illustrated in FIG. 2, for example), which couples, attaches, integrates, or otherwise is bonded to the body wire or archform 1. Moreover, the body wire or archform 1 incorporates a centrally-placed omega loop 10 with contra-loops 11. The omega loop 10 permits widening of the body wire or archform 1 as development proceeds. The contra-loops 11 prevent narrowing of the body wire or archform 1 as development proceeds. Furthermore, the body wire or archform 1 extends directly or indirectly as an occlusal rest 12 on to the occlusal (biting) surface of at least one tooth so that the upper and lower teeth are prevented from contacting as normal. Typically, this direct or indirect occlusal rest 12 is applied to the last two molar teeth in the upper jaw; however, this arrangement can be varied according to clinical presentation, especially in children.

Active Elements

Appliance 100 includes active elements adapted to provide brief doses of cyclic forces to induce sutural osteogenesis. The active elements can be vibrational, ultrasonic or oscillatory components with an actuator or other expansion mechanism, such as suture spring 9, which straddles the midline of the appliance.

In lieu of, or in addition to the active elements, the appliance 100 includes a plurality of micro-screws 2 along with a driving means. The driving means, preferably, consists of either an electrical, ultrasonic (vibrational) meso-motor, or, alternatively, a micro-motor. Other combinations, including a plurality of such meso- and micro-motors can be included in alternative embodiments of the appliance. The driving means couples to, or is otherwise located on, the body wire or archform 1.

Importantly, the driving means provides micromechanical, cyclic, tensile and/or compressive forces and/or doses of oscillatory strain. For example, the driving means adapts to apply these forces or doses of strain using an ultrasonic/vibrational component similar to that found in ultrasonic dental scalers, electric toothbrushes, ultrasonic dental cleaning appliances and cellular telephones. The range of force applied will be very low and vary between 0.1-10N although forces of other magnitudes may be applied as required. The frequency applied will vary between 1-600 Hz although other ranges of cycles may be applied as required.

In a preferred embodiment, the appliance 100 is activated for 10-60 minutes per day although other durations of application may be used as required. The overall duration of the ultrasonic/vibrational therapy will last between 5-14 consecutive days or non-consecutive days e.g. alternate days, although other durations of therapy will be used as required, depending on the patient's response.

One possible driving means includes a micro-screw 2, which adjusts manually using a mini-screwdriver, for example.

Tooth-Contacting Material

The appliance 100 further includes a tooth-contacting material 6 having high-elasticity, such as pre-formed alloys that are custom-formed to adapt to the long axis of the palatal/lingual surfaces of the teeth. These materials can be adjusted as required by the dental clinician. Accordingly, in one embodiment, an intra-oral appliance 100 attaches or couples at least two permanent or deciduous teeth using C clasps 5, bands, or direct bonding to the surfaces of the teeth with orthodontic brackets.

Clasps

One preferred embodiment includes two or more retentive C clasps 5 (or Adams or Delta or Crozat clasps) to hold the appliance in place while it is being worn. These C clasps 5 or Adams or Delta or Crozat clasps are attached to the molar or similar teeth and provide good retention. In another preferred embodiment, appliance 100 includes retentive C clasps 5 that are incorporated into the extended labial bow 3. These retentive C clasps 5 engage the mesial and distal undercuts of the molar teeth or other teeth (similar to partial denture clasps) and prevent dislodgement of appliance 100 when it is in situ. For example, as previously disclosed in Singh (U.S. Utility patent application Ser. No. 12/240,144 filed on 29 Sep. 2008) two or more retentive (Adams or Delta or Crozat) clasps hold the appliance in place while it is being worn. These Adams or Delta or Crozat clasps are attached to the molar teeth and provide good retention. However, with these current-art types of clasps attached, it is difficult if not impossible to change the orientation of the molar teeth. In contrast, in another preferred embodiment of the present invention, the Adams or Delta or Crozat clasps are replaced by C clasps 5 that fit into the undercut regions of the premolar (bicuspid) and molar teeth.

By having several C clasps 5, good retention is achieved, while providing further scope to change the position of molar teeth.

Labial Bow

In one preferred embodiment, appliance 100 includes an anterior labial bow 3 arranged across the front six teeth. In an alternate preferred embodiment, the labial bow 3 extends to the molar region with an additional U-loop 13. These extensions give appliance 100 more stability.

In yet another preferred embodiment, the labial bow 3 is constructed of an esthetic, tooth-colored, composite material that behaves in the same fashion as a stainless steel wire labial bow, yet appears almost invisible to the unwary onlooker.

Maxillary and Mandibular Devices

Figure 3:
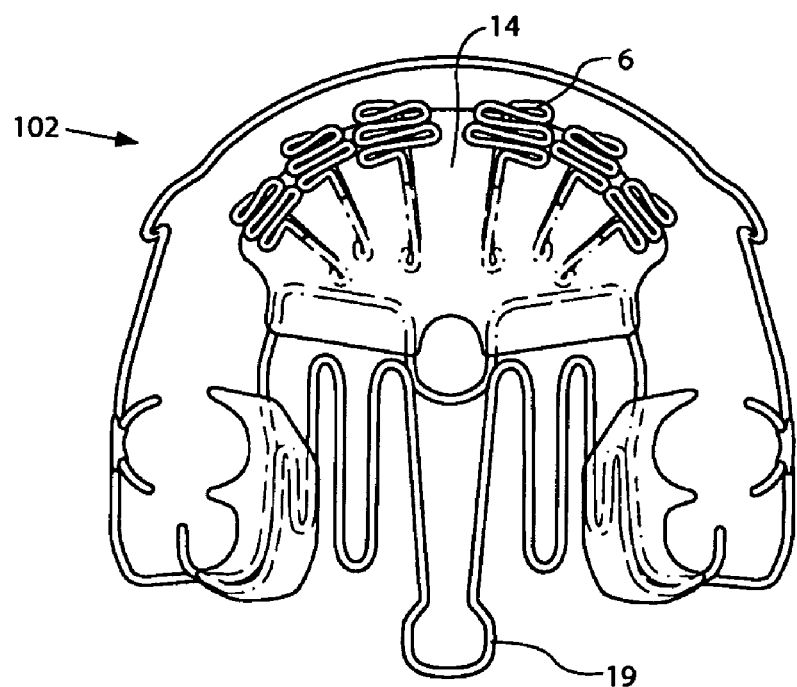
FIG. 3 is a top view of an appliance according to a third preferred embodiment of the present invention.
Figure 4:
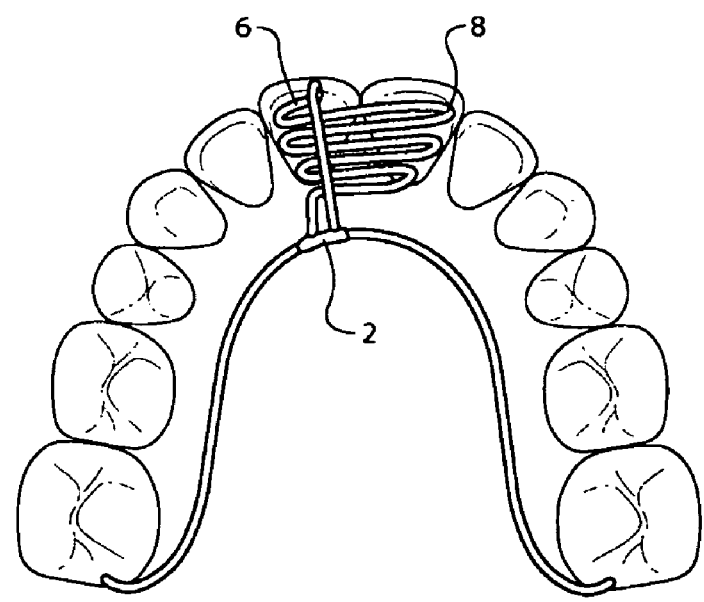
FIG. 4 is a top view of an appliance showing asymmetrical loops 8 of a three-dimensional axial spring 6, according a third preferred embodiment of the present invention.

A preferred embodiment of the invention includes a maxillary device 100, which is a specialized, non-rigid appliance adapted to lie in close approximation to the patient's tissues. Another preferred embodiment includes a mandibular device 101 (of FIG. 2 for example), which is a specialized, non-rigid appliance adapted to situate in close approximation to the patient's tissues. Yet, another preferred embodiment includes a maxillary device 102 (of FIG. 3, for example), which is a specialized, non-rigid appliance adapted to situate in close approximation to the tissues of patients diagnosed with obstructive sleep apnea.

Bite Props

Figure 6:
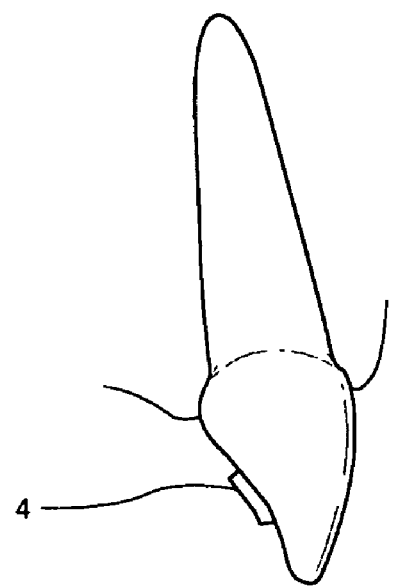
FIG. 6 is a partial side view showing a directional bite prop 4 in relationship to a tooth of a patient according to a preferred embodiment of the present invention.

In another embodiment, the appliances 100 and/or 101 and/or 102 cooperate, and are used in conjunction with directional bite props. For example, suitable bite props include bite props 4 (see for example, FIG. 6), which are made using a light-cured, bonded material (e.g. Triad® available from Dentsply International, 221 W. Philadelphia Street, York, Pa. 17405-0872, USA) to disarticulate the dentition and/or establish equilibration.

The bite props 4 prevent articulation of the dentition and/or appliance interferences from causing mandibular displacements while treatment is being provided, and permit patients to eat without an epigenetic-pneumopedic device in situ. For example, maintenance of occlusal disarticulation is achieved partly with directional bite props 4 on the palatal surface of the upper central incisors, combined with an epigenetic-pneumopedic device, which is appliance 100 and/or appliance 101 and/or appliance 102.

A treatment regime with an appliance 100 and/or 101 and/or 102, according to the teachings of the present invention using bite props 4, permits muscular and skeletal primacy in the development of an optimal maxillary/mandibular relationship—in conjunction with the establishment of a more ideal vertical facial height. In addition, bite props 4 can be used to guide mandibular displacements to a more ideal orientation; for example, alignment of the midlines and centering the mandible in the facial structure. Thus, the inclined planes of the bite props 4 provide occlusal stops and mandibular positioning clues for altering the occlusion into a more favorable skeletal and dental configuration.

The bite props 4 couple or bond directly to the appropriate teeth; for example, the upper central incisors, cuspids, or first bicuspids, although other teeth may be used as indicated. The bite props 4 can be trimmed using a green stone to correct facial height, lateral positioning, and posture of the mandible. As such, bite props 4 can be used as "directional devices" during treatment. This directional treatment and re-positioning allows genetically-encoded developmental mechanisms of pattern formation (for example, symmetry) to reactivate, eventually leading to continued growth and development via stem cells, thus correcting deficient size and asymmetry of the upper airway through non-surgical remodeling or the pneumopedic effect.

Generally speaking, the more the mandible is distalized, the deeper the bite becomes and, as this will produce airway compromise in patients, the head postures forward in an attempt to maintain an adequate, functional airway space. Therefore, throughout the entire treatment process it is important to be constantly attentive to the realignment of the mandible to the expanded maxilla, which previously occupied a restricted midfacial space (volume). The use of directional bite props 4, especially on the upper first bicuspids allows the remodeling of the cranial, maxillo-palatal and mandibular spatial matrices.

One type of suitable bite prop 4 includes a specialized cuspid prop, which is contoured to the shape of a bicuspid, and provides an esthetic compromise for adult patients. The thickness of the directional bite props 4 ranges from approximately 0.5 mm to approximately 5.0 mm, as determined by orthodontic equilibration, and may be absent in certain locations, as required.

Additionally, the directional bite props 4 of selected teeth unilaterally or bilaterally are about 1-5 mm in thickness or less. And, the vibratory signal is produced by intermittent contact of opposing teeth in the maxillary and mandibular dental arches, during sleep, swallowing, speech and mastication, for example.

In yet a further embodiment, the directional bite props 4 are replaced by an anterior acrylic bite plane 14 in appliance 100 or 101 or 102. This anterior bite plane 14 provides a tripod of support for the mandible, along with the left and right extensions of the body wire or arch form 1. Note that the anterior acrylic bite plane 14 is split in the midline to permit widening of the body wire or archform 1 as development proceeds.

In yet a further embodiment, the directional bite props 4 are replaced by a posterior acrylic bite plane 17 (as detailed in FIG. 19, for example) in appliance 100 or 101 or 102. This posterior bite plane 17 provides support for the mandible, along with the left and right extensions of the body wire or arch form 1. Note that the posterior acrylic bite plane 17 is attached to body wire or archform 1 so that suture spring 9 in the midline permits widening of appliance 100 or 101 or 102 as development proceeds.

3-D Axial Springs

In another preferred embodiment, the appliance includes three-dimensional (3-D) axial springs 6 on the anterior (front) six teeth of the appliance 100 and/or 101 in either the upper or lower arch or both constructed of round wire with a diameter of 0.018 in. These 3-D axial springs are approximately about 5 mm wide for the lower left and right anterior teeth; and approximately about 6 mm wide for the upper left and right anterior teeth, including the upper and lower cuspids (canines) and bicuspids (premolars). These six springs 6 allow good manipulation of the anterior teeth, but sometimes posterior (back) teeth are tipped towards the tongue or lingually-inclined and require correction.

In an alternative preferred embodiment, the appliance additionally includes 3-D axial springs 7 that are in contact with the premolar (bicuspid) and molar teeth. These premolar (bicuspid) and molar springs 7 can help correct the position of the premolar (bicuspid) and molar teeth, as Adams or Delta or Crozat clasps are replaced by C clasps 5 that fit into the interproximal regions between the premolar (bicuspid) and molar teeth. These premolar (bicuspid) and molar 3-D axial springs 7 produce good interdigitation of the teeth. These premolar (bicuspid) and molar 3-D axial springs 7 will have a wider transverse axis, which is approximately about 8 mm wide for the upper and lower left and right molar teeth, for example.

In one preferred embodiment, the appliance includes left- and right-handed springs. This preferred embodiment recognizes the advantages of symmetrical components and, accordingly, the geometric or configuration isomerism that describes the functional orientation of the 3-D axial springs is stereo-isomerism. Put simply, the springs are symmetrically configured and arranged about the midline, in attempt to mimic the cis- and trans-forms of amino acids that exist in the human body.

In one preferred embodiment, a mini-screw 2 keeps the 3-D axial springs 6 and/or 7 in optimal, intimate contact with the palatal/lingual tissues of a tooth as treatment proceeds.

Using a first spring design, the two central teeth in the upper or lower arch can be left without any spring contacting their surfaces, as treatment proceeds (the springs 6 are too far apart to make contact with central teeth in the midline).

In a second preferred embodiment, the springs for the central teeth in the midline have asymmetrical extensions of the transverse loops 8 of the spring that extend across the midline. Thus, these asymmetrical spring extensions 8 remain in contact with the central teeth in the midline even after the space between the two central teeth is widely separated as treatment proceeds.

In one preferred embodiment the appliance 100 and/or 101 and/or 102 includes metallic springs throughout fabricated from various alloys. In another preferred embodiment the appliance comprises springs fabricated from carbon nanotubes. These single- and multi-walled nanotubes provide the possibility of producing strong, unlimited-length wires through high-pressure nanotube linking from which the 3-D axial springs 6 and 7 and body wires/archforms 1 and suture springs 9 and lower suture springs 16 would be fabricated.

Figure 14:
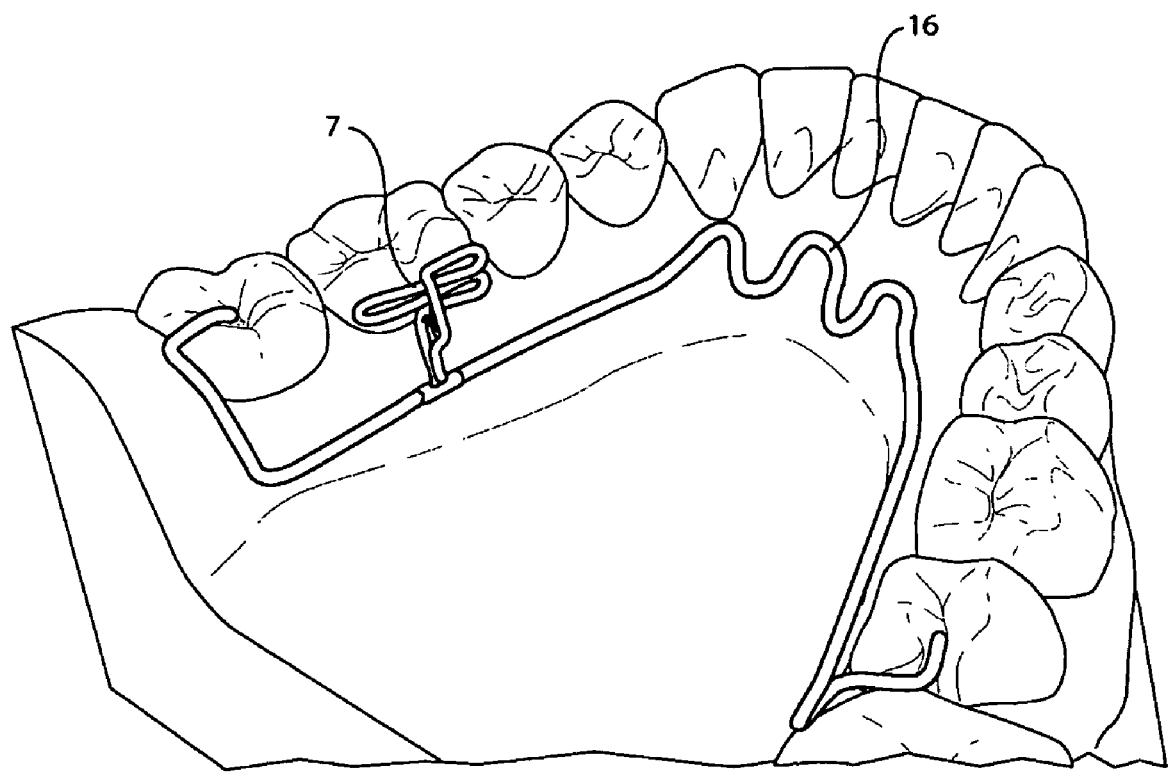
FIG. 14 is an offset top view of an appliance with a lower suture spring 16 in situ according to one preferred embodiment of the present invention.

In another preferred embodiment one or more "suture" springs 9 or coiled springs constructed of round wire with a diameter of 0.032 in. are used in conjunction with the body wire/archform 1. These "suture" springs 9 or coiled springs can be integrated or incorporated into the lower body wire/archform and lower suture spring 16 (as FIG. 14 illustrates, for example) as well as the upper body wire/archform 1.

Figure 12:
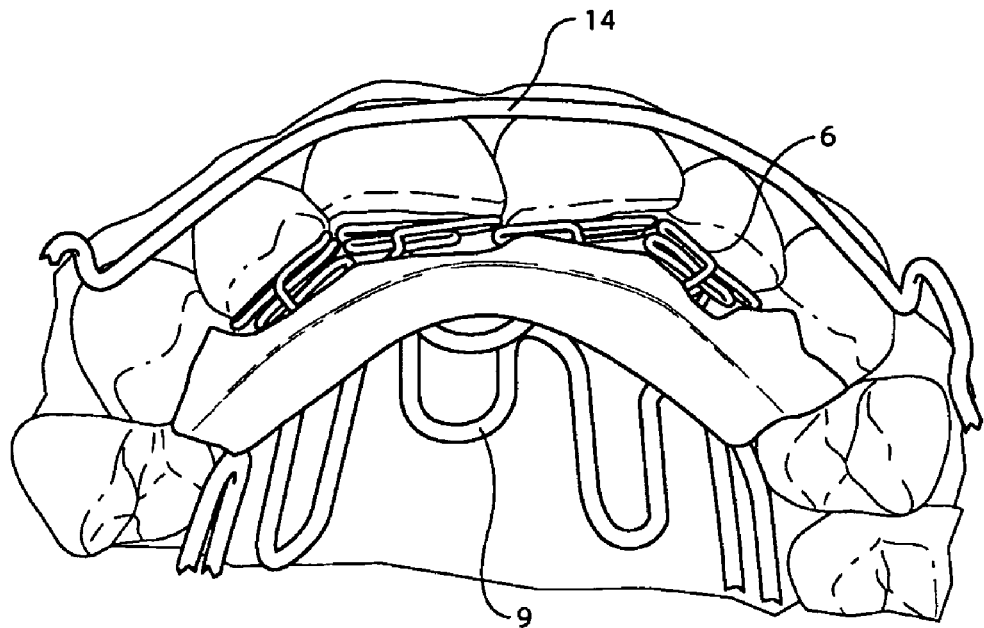
FIG. 12 is a view of an appliance with anterior 3-D axial springs 6 in situ according to one preferred embodiment of the present invention.
Figure 13:
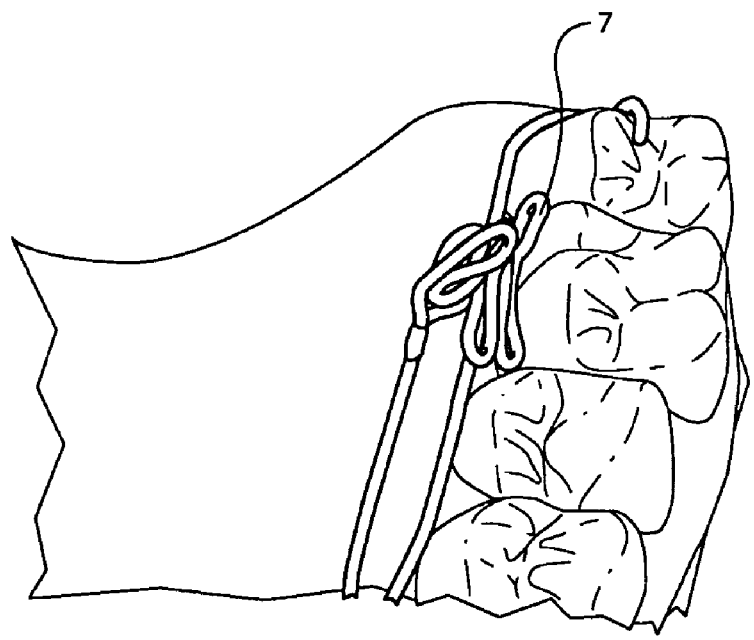
FIG. 13 is a top view of an appliance with a molar axial spring 7 in situ according to one preferred embodiment of the present invention.

In yet another preferred embodiment the axes of the 3-D springs 6 (as FIG. 12 illustrates, for example) and 7 (as FIG. 13 illustrates, for example) are oriented in three directions including a transverse axis (from side to side across the tooth), an antero-posterior axis (from the front biting edge of the tooth back towards the gum), and a vertical axis (spring loops extending up away from the tooth, and down towards the tongue). The orientation of these vertical spring loops 18 is orientated by 90-degrees from near the tooth surface to away from the tooth surface. The spring loops 18 look like a mattress spring. In this orientation, forces will be absorbed by vertical compression of the spring loops during function. This compression will be stored as potential energy in the compressed spring loops. When the force is removed, this potential energy will be dissipated as kinetic energy. This kinetic or vibrational movement of the 3-D axial spring will act as a mechanical signal on the tooth surface. These mechanical signals will undergo signal transduction and result in gene transcription. These transcribed genes will biosynthesize new bone, including via stem cells, which will be remodeled, eventually allowing correction of tooth position and non-surgical upper airway remodeling i.e. the pneumopedic effect.

It should be noted that the configuration of spring loops 18 in the present invention differs from the spring loops previously disclosed in this same inventor's earlier invention (U.S. Utility patent application Ser. No. 12/240,144 filed on 29 Sep. 2008) as biting forces are exerted along the long-axis of the vertical spring loops 18. And, in this orientation the spring loops resist these forces, rather than absorb them. Further, as disclosed previously, two parallel arms of the 3-D axial spring are embedded in the acrylic baseplate. Although this design permits the spring to be well attached to the device, continuing tooth movement causes the spring to lose contact with the tooth surface. Thus, the spring has to be bent or distorted to maintain contact with the tooth. By bending or distorting the 3-D axial spring, the configuration of the spring is effectively destroyed, producing a less than effective spring.

Figure 5:
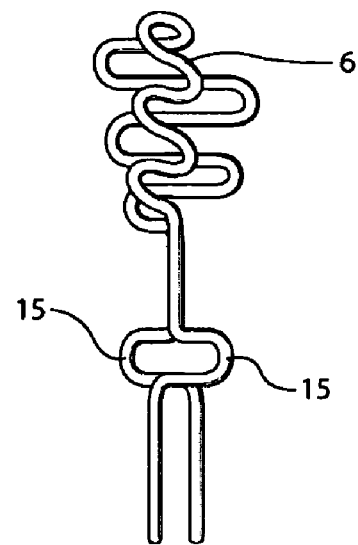
FIG. 5 is a top view of an appliance showing C-loops 15 in a 3-D axial spring 6.

In yet another preferred embodiment described here, the two parallel arms of the 3-D axial springs 6 and 7 attached to the body wire/archform 1 have at least one or more "C loops" 15 (as FIG. 5 illustrates, for example) along their length. These C-shaped loops 15 are compressed by the clinician using orthodontic pliers to effectively elongate the two parallel arms of the spring, keeping the spring is close approximation to the tooth surface while preserving the configuration of the 3-D axial springs 6 and 7.

Figure 7:
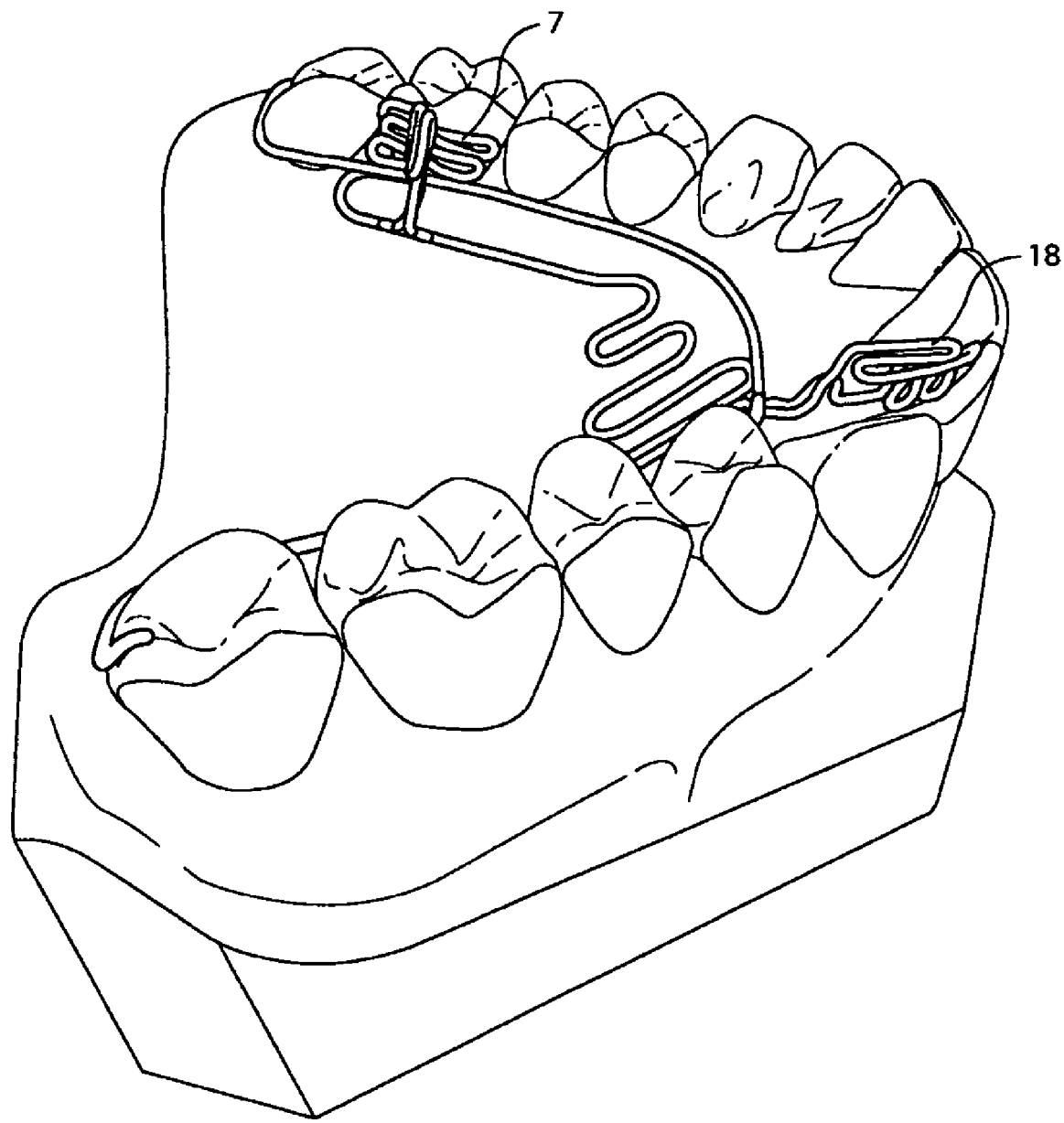
FIG. 7 is a partial side view showing loops of a 3-D axial spring 6 of the appliance of FIG. 1 in relationship to a tooth of a patient.

As previously disclosed by Singh, springs 6 are located on the anterior (front) six teeth of the appliance in either the upper or lower arch. These six springs, which are approximately: 5 mm wide for the lower left anterior teeth; 5 mm wide for the lower right anterior teeth; 6 mm wide for the upper left anterior teeth, including the upper and lower cuspids (canines); 6 mm wide for the upper right anterior teeth, including the upper and lower cuspids (canines), allow good manipulation of the anterior teeth, but sometimes posterior (back) teeth are tipped towards the tongue or lingually-inclined and require correction. Accordingly, in yet another preferred embodiment of the present invention the 3-D axial springs contact the premolar (bicuspid) and molar teeth, as necessary. These premolar (bicuspid) and molar springs 7 (as FIG. 7 illustrates, for example) help correct the position of the premolar (bicuspid) and molar teeth. These premolar (bicuspid) and molar springs 7 can help produce good interdigitation of the teeth. Further, the premolar (bicuspid) and molar 3-D springs have a wider Transverse axis, which is approximately: 6 mm wide for the upper left bicuspids (premolars); 6 mm wide for the upper right bicuspids (premolars); 8 mm wide for the upper and lower left molar teeth; and 8 mm wide for the upper and lower right molar teeth.

Singh previously disclosed that it was not mandatory to have left- and right-handed springs. However, in yet another embodiment of the present invention, the geometric or configuration isomerism that describes the functional orientation of the springs is stereo-isomerism. Put simply, the springs are symmetrically configured and arranged about the midline, in attempt to mimic the cis and trans forms of amino acids that exist in the human body.

Also, Singh previously disclosed a midline jackscrew to separate two halves of an acrylic baseplate. This previous device, however, may result with the two central teeth in the upper or lower arch without any spring contacting their surfaces, as the baseplate halves are too far apart to make contact with central teeth in the midline. Accordingly, in yet another preferred embodiment of the present invention the springs for the central teeth in the midline have asymmetrical extensions of the transverse loops 8 of a spring that extends across the midline. Thus, these asymmetrical spring extensions 8 remain in contact with the central teeth in the midline even after the space between the two central teeth is widely separated as treatment proceeds.

As further disclosed by Singh, a midline jack-screw was used to separate the two halves of the acrylic baseplate as treatment proceeds. However, in some cases antero-posterior (front to back) development may be required instead of transverse development. To address this requirement, in yet another preferred embodiment of the present invention a similar midline jack-screw is augmented by an actuator or jack-screw that lies transversely to produce antero-posterior development. In yet another embodiment, a 3-way screw may be suitably deployed to provide antero-posterior and/or transverse development.

In the previous design of Singh, the jack-screw required periodic adjustment as treatment proceeded. This adjustment caused difficulty for some patients and sometimes the screw was turned too much, turned the wrong way or not turned at all. To address this inconsistency, the present invention in yet another preferred embodiment replaces the current-art midline jackscrew with one or more suture springs 9. The suture spring 9 separates the body wire/archform 1 as treatment proceeds without needing adjustment by the patient. However, the omega loop and contra-loops may require adjustments by the treating clinician. In addition, these suture springs 9 can be incorporated or integrated into the lower body wire/archform 1, which includes an omega loop and contra-loops, as well as being placed on the upper body wire/archform 1.

In the previous design of Singh, the jack-screw adjustment caused difficulty for some patients as further development was needed even after the jackscrew had reached the full extent of its travel. To address this inadequacy, in the present invention in yet another preferred embodiment the current-art midline jack-screw is replaced by one or more suture springs 9 when the jack-screw has reached the full extent of its travel. The new suture spring 9 separates the body wire/archform 1 as further treatment proceeds without needing adjustment by the patient. However, the omega loop and contra-loops may require adjustments by the treating clinician. In addition, these suture springs 9 can be incorporated or integrated into the lower body wire/archform 1, which includes an omega loop and contra-loops, as well as being placed on the upper body wire/archform 1.

In yet another embodiment described here and as FIG. 7 shows, the 3-D springs 6 and 7 and body wires/archforms 1 and suture spring 9 are fabricated from carbon nanotubes. These single- and multi-walled nanotubes provide the possibility of producing strong, unlimited-length wires through high-pressure nanotube linking from which the springs would be fabricated.

In an alternative preferred embodiment, the appliance includes 3-D axial springs 7 that are in contact with the premolar (bicuspid) and molar teeth. These premolar (bicuspid) and molar springs 7 can help correct the position of the premolar (bicuspid) and molar teeth, as Adams or Delta or Crozat clasps are replaced by C-clasps 5 that fit into the undercut regions of the premolar (bicuspid) and molar teeth. These premolar (bicuspid) and molar 3-D axial springs 7 can help produce good interdigitation of the teeth. These premolar (bicuspid) and molar 3-D axial springs 7 will have a wider transverse axis, which is approximately about: 6 mm wide for the bicuspids (premolars); and about 8 mm wide for the upper and lower left and right molar teeth, for example.

In one preferred embodiment, a mini-screw 2 keeps the 3-D axial spring 6 and/or 7 in optimal, intimate contact with the palatal/lingual tissues of a tooth as treatment proceeds.

As disclosed in U.S. Utility patent application Ser. No. 12/240,144 filed on 29 Sep. 2008 by Singh (the entire disclosure of which is expressly incorporated herein by reference as if fully set forth), two parallel arms of a 3-D axial spring are embedded in an acrylic baseplate. While this design permits the spring to be well attached to the acrylic baseplate, one limitation of this design is that with continuing tooth movement the spring becomes disengaged from the tooth and does not maintain contact with the tooth surface: Thus, the spring has to be adjusted or otherwise bent or distorted to maintain contact with the tooth, and such manipulation must be performed by a trained clinician. Further, by bending or distorting the 3-D axial spring, the configuration of the spring is effectively destroyed, producing a less than effective spring. In contrast, the present invention in a preferred embodiment includes two parallel arms with a 3-D axial spring 6, 7 attached, the arms couple or otherwise attach to a body wire/archform 1 and further have at least one or more "C loops" 15 along their length (as FIGS. 5 and 1 detail, for example). These C-loops 15 can be compressed by the clinician using orthodontic pliers to effectively elongate the two parallel arms of the spring 6, 7, keeping the spring in close approximation to the tooth surface, while preserving the configuration of the 3-D axial spring 6, 7.

Again, the current-art, as disclosed for example in Singh (U.S. Utility patent application Ser. No. 12/240,144) springs are located on the anterior (front) six teeth of the current-art appliance in either the upper or lower arch. These six springs allow good manipulation of the anterior teeth, but sometimes posterior (back) teeth are tipped towards the tongue or lingually-inclined and require correction. To better address this common problem, another preferred embodiment of the present invention includes a plurality of 3-D axial springs 7 placed in contact with the premolar (bicuspid) and molar teeth, as necessary. Accordingly, these springs 7 include a proximal end adapted to contact an adjacent tooth, and an oppositely disposed distal end, adapted to couple to the body wire/archform 1. Further, these premolar (bicuspid) and molar springs 7 help correct the position of the premolar (bicuspid) and molar teeth and produce good interdigitation of the teeth. These premolar (bicuspid) and molar 3-D springs 7 have a wider Transverse axis, which is approximately about 6 mm wide for the upper left bicuspids (premolars); about 6 mm wide for the upper right bicuspids (premolars); and about 8 mm wide for the upper and lower left molar teeth; and about 8 mm wide for the upper and lower right molar teeth, for example.

Singh also discloses the use of symmetrical springs (U.S. Utility patent application Ser. No. 12/240,144) and notes that it was not mandatory to have left- and right-handed springs. However, symmetry and symmetrical designs abound in nature and, accordingly, in yet another embodiment of the present invention, the geometric or configuration isomerism that describes the functional orientation of the springs is stereo-isomerism. Put simply, the springs are symmetrically configured and arranged about the midline, in attempt to mimic the cis- and trans-forms of amino acids that exist in the human body.

The current-art of Singh (U.S. Utility patent application Ser. No. 12/240,144) also discloses the use of a midline jackscrew to separate and enable adjustment of two halves of the acrylic baseplate as treatment proceeds. However, one possible shortcoming of this current-art device is that two central teeth in the upper or lower arch can be left without any spring contacting their surfaces when the baseplate halves are too far apart to make contact with central teeth in the midline. To address this, another preferred embodiment of the present invention includes midline springs (for the central teeth) having asymmetrical extensions of transverse loops 8 extending across the midline. Thus, these asymmetrical spring extensions remain in contact with the central teeth in the midline even after the space between the two central teeth is widely separated as treatment proceeds.

The prior Singh-device utilizes a midline jack-screw to separate two halves of the acrylic baseplate as treatment proceeds. However, this screw required purposeful adjustment (turning by either the patient or caregiver) during the treatment progression. This proves problematic as some patients/parents find it difficult to turn the screw, the screw is turned too much, turned the wrong way, or not turned at all. The present invention overcomes this limitation by replacing the current-art midline jack-screw with one or more suture springs 9 (as detailed by FIG. 12, for example) that separate the body wire/archform 1, which includes an omega loop and contra-loops that are adjusted by the treating clinician as treatment proceeds, without a screw needing to be adjusted by the patient. These suture springs 9 can be incorporated or integrated into the lower body wire/archform as well as being placed within the upper arch.

Other Uses of Devices, Systems, and Treatment Methods

The appliance 100 and 101 and 102 adapts for use with conventional fixed orthodontic appliances (braces), if required, as well as orthodontic headgear, such as a facemask, if indicated. It may also be used as a component in a two-phase orthopedic-orthodontic treatment, and is suitable for children, teenagers, and adult dental patients.

In another preferred embodiment, the appliance 102 includes an Extended suture spring 19 in which the midline loop is extended by approx. 0.5 in to 2 in (1-4 cm) in length. This extended suture spring 19 is reserved for use in patients diagnosed with obstructive sleep apnea. In these patients the tongue assumes a low posture when the patient is lying on the back during sleep, and obstructs the upper airway. In this preferred embodiment of the appliance 102, the extended suture spring 19 contacts the tongue, and through proprioception guides the tongue upwards and forwards, preventing the obstructive event.

In another preferred embodiment, the extended suture spring 19 has, at least one but preferably, a plurality of undulations or C loops along its length to help a clinician adjust the extended suture spring to the correct clinical length.

In another preferred embodiment, the extended suture spring is attached to a baseplate (preferably an acrylic baseplate) to prevent the abnormal positioning of the tongue, and to help a clinician adjust the extended suture spring 19 to the correct clinical length.

In another preferred embodiment, the extended suture spring is attached to the acrylic baseplate via screw system to prevent the abnormal positioning of the tongue, and to help a clinician adjust the extended suture spring 19 to the correct clinical length by turning the screw.

In another preferred embodiment, the extended suture spring 19 is augmented by self-cure acrylic or other suitable materials to help a clinician adjust the length and shape of the extended suture spring 19 to the correct clinical length, to prevent the abnormal positioning of the tongue, In another preferred embodiment, the appliance includes 3-D axial springs 6, 7 on the body wire of the Advanced Lightwire Functional (ALF) appliance in either the upper or lower arch or both.

In another preferred embodiment, the appliance includes 3-D axial springs 6, 7 on an archform in the Basic Maxillary Crozat appliance in the upper arch.

In another preferred embodiment, the appliance includes 3-D axial springs 6, 7 on an archform in the Interceptive Crozat appliance in the upper or lower arch or both.

In another preferred embodiment, the appliance includes 3-D axial springs 6, 7 on an archform in the Phase I Crozat appliance in the upper or lower arch or both.

In another preferred embodiment, the appliance includes 3-D axial springs 6, 7 on an archform in the Basic Mandibular Crozat appliance in the lower arch.

In another preferred embodiment, the appliance includes 3-D axial springs 6, 7 on an archform in the FR (Fixed/Removable) Crozat appliance in the upper or lower arch or both.

In another preferred embodiment, the appliance includes 3-D axial springs 6, 7 on an archform in the Porter appliance in the upper arch.

In another preferred embodiment, the appliance includes 3-D axial springs 6, 7 on an archform in a Quad Helix appliance in the upper arch.

In another preferred embodiment, the appliance includes 3-D axial springs 6, 7 on the anterior arch wires in the Wilson 3D® Multi-Action Palatal appliance in the upper arch.

In another preferred embodiment, the appliance includes 3-D axial springs 6, 7 on the anterior arch wires in the Wilson 3D® Quad Helix appliance in the upper arch.

In another preferred embodiment, the appliance includes 3-D axial springs 6, 7 on the anterior arch wires in the 3D® Quad-Action Mandibular appliance in the lower arch.

In another preferred embodiment, the appliance includes 3-D axial springs 6, 7 on an archform in the Nitanium Palatal Expander appliance in the upper arch.

In another preferred embodiment, the appliance includes 3-D axial springs 6, 7 on an archform in the Fixed "Fan-Screw" RPE appliance in the upper arch.

In another preferred embodiment, the appliance includes 3-D axial springs 6, 7 on the anterior arch wire in the Clark Trombone and Lingual Arch Developer (LAD) appliance in the lower arch.

In another preferred embodiment, the appliance includes 3-D axial springs 6, 7 on an archform in the Cantilevered Herbst appliance in the upper arch or lower arch or both.

In another preferred embodiment, the appliance includes 3-D axial springs 6, 7 on an archform in the Rick-A-Nator appliance in the upper arch.

In another preferred embodiment, the appliance includes 3-D axial springs 6, 7 on an archform in the Rick-A-Nator 2 appliance in the upper arch.

In another preferred embodiment, the appliance includes 3-D axial springs 6, 7 on an archform in the Removable Rick-A-Nator 2 appliance in the upper arch.

In another preferred embodiment, the appliance includes 3-D axial springs 6, 7 on an archform in the Modified Rick-A-Nator appliance in the upper arch.

In another preferred embodiment, the appliance includes 3-D axial springs 6, 7 on an archform in the Inclined Plane appliance in the upper arch.

In another preferred embodiment, the appliance includes 3-D axial springs 6, 7 on the anterior arch wire in the Inter-Oral Face Mask appliance in the upper arch.

In another preferred embodiment, the appliance includes 3-D axial springs 6, 7 on an archform in the Bonded Maxillary Face Mask Expansion appliance in the upper arch.

In another preferred embodiment, the appliance includes 3-D axial springs 6, 7 on an archform in the 3D® Maxillary Bimetric Distalizing Arch appliance in the upper or lower arch or both.

In another preferred embodiment, the appliance includes 3-D axial springs 6, 7 on the anterior arch wire in the 3D® Lingual Arch appliance in the lower arch.

In another preferred embodiment, the appliance includes 3-D axial springs 6, 7 on an archform in the 3D® Nance appliance in the upper arch.

In another preferred embodiment, the appliance includes 3-D axial springs 6, 7 on the anterior arch wire in the 3D® Quad-Helix appliance in the upper arch.

In another preferred embodiment, the appliance includes 3-D axial springs 6, 7 on the anterior arch wire in the 3D® Quad-Action Mandibular appliance in the lower arch.

In another preferred embodiment, the appliance includes 3-D axial springs 6, 7 on the anterior arch wire in the 3D® Multi-Action Palatal appliance in the upper arch.

In another preferred embodiment, the appliance includes 3-D axial springs 6, 7 on the anterior arch wire in the Clark Trombone appliance in the upper or lower arch or both.

In another preferred embodiment, the appliance includes 3-D axial springs 6, 7 on the labial arch of a Labial-Lingual appliance in either the upper or lower arch or both.

In another preferred embodiment, the appliance includes 3-D axial springs 6, 7 on an archform on a High Palate Rapid Palatal Expansion appliance in the upper arch.

In another preferred embodiment, the appliance includes 3-D axial springs 6, 7 on an archform on a Direct Bond Suture Expansion appliance in the upper arch.

In another preferred embodiment, the appliance includes 3-D axial springs 6, 7 on an archform on a Fan-Type Rapid Palatal Expansion appliance in the upper arch.

In another preferred embodiment, the appliance includes 3-D axial springs 6, 7 on the NiTi wire of the Williams Expander appliance in the lower arch.

In another preferred embodiment, the appliance includes 3-D axial springs 6, 7 on an archform in the Fixed Lingual Expansion appliance (FLEA) in the lower arch.

In another preferred embodiment, the appliance includes 3-D axial springs 6, 7 on the tubing of the Arnold Expander appliance in either the upper or lower arch or both.

In another preferred embodiment, the appliance includes 3-D axial springs 6, 7 on an archform in the Haas Memory Transverse Expansion appliance in the upper arch.

In another preferred embodiment, the appliance includes 3-D axial springs 6, 7 on an archform in the Dillingham Habit-Expansion appliance in the upper arch.

In another preferred embodiment, the appliance includes 3-D axial springs 6, 7 on an archform in the Haas Suture Expanding appliance in the upper arch.

In another preferred embodiment, the appliance includes 3-D axial springs 6, 7 on an archform in the Rapid Palate Expansion 4-Banded Hyrax appliance in the upper arch.

In another preferred embodiment, the appliance includes 3-D axial springs 6, 7 on an archform in the High Palate Rapid Palate Expansion Hyrax type appliance in the upper arch.

In another preferred embodiment, the appliance includes 3-D axial springs 6, 7 on an archform in the Rapid Palate Expansion Super Screw appliance in the upper arch.

In another preferred embodiment, the appliance includes 3-D axial springs 6, 7 on an archform instead of lap springs in a Bonded Rapid Palate Expansion appliance with Rests in the upper arch.

In another preferred embodiment, the appliance includes 3-D axial springs 6, 7 on an archform instead of lap springs in a Bonded Rapid Palate Expansion appliance in the upper arch.

In another preferred embodiment, the appliance includes 3-D axial springs 6, 7 on the anterior arch wire of the Anterior/Posterior Fixed Sagittal appliance in either the upper arch.

In another preferred embodiment, the appliance includes 3-D axial springs 6, 7 on an archform in the M Pendulum appliance in the upper arch.

In another preferred embodiment, the appliance includes 3-D axial springs 6, 7 on the anterior arch wire of the Lower Trombone appliance in the lower arch.

In another preferred embodiment, the appliance includes 3-D axial springs 6, 7 on an archform in the Fixed Unilateral Distalizer appliance in the upper arch.

In another preferred embodiment, the appliance includes 3-D axial springs 6, 7 on the anterior arch wire of the CD Distalizer appliance in either the upper or lower arch or both.

In another preferred embodiment, the appliance includes 3-D axial springs 6, 7 on an archform in the Modified CD Distalizer appliance in the upper arch.

In another preferred embodiment, the appliance includes 3-D axial springs 6, 7 on an archform in the Magill Sagittal to Advance appliance in the upper arch.

In another preferred embodiment, the appliance includes 3-D axial springs 6, 7 on an archform in the Magill Sagittal to Distalize appliance in the upper arch.

In another preferred embodiment, the appliance includes 3-D axial springs 6, 7 on an archform in the Modified Lateral and AP Arnold appliance in either the upper or lower arch or both.

In another preferred embodiment, the appliance includes 3-D axial springs 6, 7 on an archform in the Pendex/Hilgers Pendulum appliance in the upper arch.

In another preferred embodiment, the appliance includes 3-D axial springs 6, 7 on an archform in the "M" Pendex appliance in the upper arch.

In another preferred embodiment, the appliance includes 3-D axial springs 6, 7 on an archform in the Grumrax appliance in the upper arch.

In another preferred embodiment, the appliance includes 3-D axial springs 6, 7 on an archform in the Snodgrass appliance in the upper arch.

In another preferred embodiment, the appliance includes 3-D axial springs 6, 7 on an archform in the Multi-Action Hyrax appliance in the upper arch.

In another preferred embodiment, the appliance includes 3-D axial springs 6, 7 on an archform in the Modified Haas Expander appliance in the upper arch.

In another preferred embodiment, the appliance includes 3-D axial springs 6, 7 on the lap springs of the Upper Jackson appliance in the upper arch and 3-D axial springs 6, 7 on the lap springs of the Lower Jackson appliance in the lower arch.

In another preferred embodiment, the appliance includes 3-D axial springs 6, 7 on an archform in the Lower Posterior Expansion appliance in the lower arch.

In another preferred embodiment, the appliance is used in conjunction with myofunctional therapy or oral myology, forming a Daytime Nighttime Appliance™ protocol, whereby the patient elects to wear the appliance for 12-16 hrs per day i.e. during the evening and at nighttime, and follows a routine of orofacial exercises as prescribed by a myofunctional therapist or certified oral myologist.

There may be other appliances known by those skilled in the art that are not specifically noted above, which would gain beneficial functionality by the addition of 3-D axial springs 6, 7.

Although the invention has been particularly shown and described with reference to certain embodiments, it will be understood by those skilled in the art that various changes in form and detail may be made without departing from the spirit and scope of the invention.

I claim:

1. A pneumopedic-orthodontic appliance for inducing remodeling of craniofacial hard and soft tissues, the appliance comprising:
 a removable oral framework consisting of a continuous body wire/archform wherein the continuous body wire/archform incorporates an omega loop in the midline with contiguous contra-loops, and includes extensions adapted to overlay an occlusal surface of posterior teeth bilaterally;
 a contacting material adapted to contact a tooth, the contacting material is coupled to the archform and is adapted to contact the palatal/lingual surface of at least one tooth; wherein the contacting material having the ability to produce and transmit intermittent, cyclic signals and wherein the contacting material comprises at least one 3-D axial spring;
 a midline suture spring, which permits separation of said archform, wherein the archform includes a plurality of archform-C-clasps, which are anchored to said archform and are adapted to attach to said posterior teeth bilaterally;
 an anterior split acrylic bite plane, which extends over said archform and said contacting material; and
 a wrap-round labial bow having at least one bow-C-clasp for retention and U loops for adjustability.

2. A pneumopedic-orthodontic appliance adapted to induce remodeling of craniofacial hard and soft tissues and tissue spaces including teeth, a palate in an upper arch and a lingual mucosa of a lower arch, the appliance comprising:
 an oral appliance comprising a continuous body wire/archform having a midline, the continuous body wire/archform incorporating an omega loop disposed at the midline with at least one contiguous contra-loop, and the continuous body wire/archform being adapted to extend or overlay the palate in the upper arch and the lingual mucosa of the lower arch;
 at least one directional bite prop adapted to arrange on an occlusal surface of selected teeth either unilaterally or bilaterally;
 a tooth-contacting material coupled to the continuous body wire/archform, the tooth-contacting material being adapted to contact a palatal/lingual surface of at least one tooth wherein the tooth-contacting material has the ability to produce and transmit intermittent, cyclic signals to said palatal/lingual surface of said tooth and wherein the tooth-contacting material comprises at least one 3-D axial spring;
 a midline suture spring being adapted to permit separation of the continuous body wire/archform, further comprising at least one archform-C-clasp coupled to the continuous body wire/archform wherein the continuous body wire/archform is adapted to attach to posterior teeth bilaterally;
 an anterior split biteplane extending over the continuous body wire/archform and the tooth contacting materials; and
 a wrap-round labial bow with at least one bow-C-clasp for retention and at least one U-loop for adjustability.

3. The appliance of claim 2 wherein the contacting material further comprises:
 a lever arm of a vibrational meso-motor capable of producing intermittent, cyclic signaling.

4. The appliance of claim 2 wherein the contacting material further comprises:
 a means for creating a vibratory signal which is adapted to contact the palatal/lingual surface of one tooth, the means for creating a vibratory signal further comprising ultrasonic technology and the means for creating a vibratory signal couples to the continuous body wire/archform.

5. The appliance of claim 4 wherein the ultrasonic technology comprises:
 an actuator consisting of a suture spring disposed to straddle a midline of the appliance.

6. The appliance of claim 4 wherein the ultrasonic technology comprises:
 at least one of the following, an ultrasonic (vibrational) meso-motor or a micro-motor.

7. The appliance of claim 4 wherein the ultrasonic technology comprises:
 a plurality of micromechanical vibrational motors.

8. The appliance of claim 2 further comprising:
 an extended midline suture spring adapted for the transient managements of patients diagnosed with obstructive sleep apnea.

* * * * *